United States Patent [19]

Drent

[11] Patent Number: 4,590,311
[45] Date of Patent: May 20, 1986

[54] PROCESS FOR THE PREPARATION OF 1,4-BUTANEDIOL

[75] Inventor: Eit Drent, Amsterdam, Netherlands

[73] Assignee: Shell Oil Company, Houston, Tex.

[21] Appl. No.: 664,128

[22] Filed: Oct. 24, 1984

[30] Foreign Application Priority Data

Dec. 29, 1983 [NL] Netherlands ................... 8304475

[51] Int. Cl.$^4$ .................... C07C 29/16; C07C 31/20
[52] U.S. Cl. ..................................... 568/852; 568/455
[58] Field of Search .......................... 568/852, 909

[56] References Cited

U.S. PATENT DOCUMENTS

| 3,239,566 | 3/1966 | Slaugh et al. | 568/909 |
| 3,527,809 | 9/1970 | Pruett et al. | 568/909 |
| 4,219,684 | 8/1980 | Imai | 568/909 |
| 4,263,449 | 4/1981 | Saito et al. | 568/883 |

Primary Examiner—J. E. Evans
Attorney, Agent, or Firm—Ronald R. Reper

[57] ABSTRACT

A process for preparation of 1,4-butanediol comprises reaction of allyl alcohol with carbon monoxide and hydrogen in the presence of a soluble rhodium catalyst, certain phosphine promoters and certain carbonitriles as solvent.

4 Claims, No Drawings

PROCESS FOR THE PREPARATION OF 1,4-BUTANEDIOL

BACKGROUND OF THE INVENTION

The invention relates to a process for the preparation of 1,4-butanediol by reaction of allyl alcohol with carbon monoxide and hydrogen in the presence of a soluble rhodium catalyst, a phosphine promoter and a solvent.

1,4-Butanediol is a valuable commercial product which finds application on a large scale, in particular as intermediate in the preparation of polyesters, polyurethanes, butyrolactone and tetrahydrofuran.

The commercial production of 1,4-butanediol relies virtually exclusively on the Reppe process, in which acetylene and formaldehyde are converted into 2-butyn-1,4-diol, which is hydrogenated to form 1,4-butanediol. In order to avoid the drawbacks involved in the use of acetylene in the Reppe process, a number of other pocesses have been proposed of which, according to Chemical Economy and Engineering Review, September 1980, 12 (No. 9), pp. 32–35, the one based on hydroformylation of allyl alcohol is the most attractive process for use on an industrial scale.

In this process—as described for instance in U.K. Patent Specification No. 1493154—allyl alcohol is first converted into hydroxybutyraldehyde by hydroformylation using a rhodiumcarbonyl complex as catalyst, an excess of a phosphine ligand and an organic solvent which is immiscible with water. Then the hydrobutyraldehyde formed is extracted from the organic solvent with water and subsequently hydrogenated to form 1,4-butanediol.

In the U.K. Patent Specification No. 1565719 a process is described in which allyl alcohol is converted direct into 1,4-butanediol in yields of up to 50%, by reacting the allyl alcohol with carbon monoxide and hydrogen in the presence of a rhodium catalyst and a tertiary phosphine containing at least one aliphatic hydrocarbyl group. In this process a solvent can advantageously be used which optionally may be immiscible with water and from which the 1,4-butanediol can be recovered by extraction with water.

It has now surprisingly been found that allyl alcohol can be converted direct into 1,4-butanediol in higher yields than mentioned in U.K. Patent Specification No. 1565719, when the reaction of allyl alcohol with carbon monoxide and hydrogen is carried out in the presence of a rhodium catalyst in combination with a trialkyl phosphine as ligand and certain carbonitriles—which will be defined hereinafter—as solvents.

SUMMARY OF THE INVENTION

The invention therefore relates to a process for the preparation of 1,4-butanediol by reaction of allyl alcohol with carbon monoxide and hydrogen in the presence of a soluble rhodium catalyst, a tertiary phosphine and a solvent, characterized in that the tertiary phosphine is a phosphine of the general formula $$P[(CH_2)_nR^1][(CH_2)_nR^2][(CH_2)_nR^3],$$

wherein $R^1$, $R^2$ and $R^3$ each represent hydrogen and n is 1 or 2, or wherein $R^1$, $R^2$ and $R^3$ each represent a substituted or unsubstituted alkyl group and n is 2 and the solvent is a carbonitrile of the general formula $$R^4CH_2CH_2CH_2C\equiv N,$$

wherein $R^4$ represents hydrogen or a substituted or unsubstituted hydrocarbyl group.

DESCRIPTION OF PREFERRED EMBODIMENTS

The soluble rhodium catalyst which can be used according to the invention comprises one or more rhodium compounds which are soluble in the reaction mixture or which in situ form soluble compounds therein. Examples of such rhodium compounds are rhodium oxide rhodium nitrate, rhodium sulphate, rhodium acetate, rhodium butyrate rhodium naphthenate, rhodium carbonyl complexes, such as dirhodiumoctacarbonyl tetrarhodiumdodecacarbonyl and hexarhodiumhexadecacarbonyl, rhodiumdicarbonyl acetylacetonate and bis(rhodiumcarbonyl chloride) and rhodiumcarbonylphosphine complexes, such as hydridorhodiumtri-(tri-n-butylphosphine)carbonyl and rhodium di(tri-n-hexylphosphine)carbonyl chloride.

The quantity of rhodium compound may vary within wide limits. Generally the quantities used are such that per mol allyl alcohol the reaction mixture comprises $10^{-4}$ to $10^{-1}$ gram atom rhodium. Preference is given to the presence of $10^{-3}$ to $10^{-2}$ gram atom rhodium per mol allyl alcohol.

The tertiary phosphine used in combination with the rhodium catalyst as ligands are represented by the general formula $$P[(CH_2)_nR^1][(CH_2)_nR^2][(CH_2)_4R^3],$$

wherein $R^1$, $R^2$ and $R^3$ are linear terminally bonded alkyl groups containing not more than 16, but preferably 2, 3, 4, 5 or 6 carbon atoms and n equals 2, or wherein $R^1$, $R^2$ and $R^3$ each represent hydrogen and n is 1 or 2. Specific examples of suitable phosphines are trimethylphosphine, triethylphosphine, tri-n-propylphosphine, tri-n-butylphosphine, tri-n-hexylphosphine, tri-n-octylphosphine, dimethylphosphine, di-n-butyloctadecylphosphine, di-n-pentylethylphosphine, tri-n-octadecylphosphine, tri-n-dodecylphosphine and tri-n-decylphosphine.

The reaction can be carried out in the presence of as little as about 3 mol phosphine per gram atom rhodium, but it is preferred to use at least 5 mol phosphine per gram atom rhodium.

As solvents are used in the process according to the invention carbonitriles of the general formula $$R^4CH_2CH_2CH_2C\equiv N,$$

wherein $R^4$ represents hydrogen or a hydrocarbyl group which may or may not be substituted, in particular an alkyl group containing up to about 10 carbon atoms in particular up to about 8 carbon atoms. Examples of suitable carbonitriles are propane carbonitrile, butane carbonitrile, heptane carbonitrile, octane carbonitrile, decane carbonitrile, undecane carbonitrile, tridecane carbonitrile, 1,5-pentane dicarbonitrile and 1,8-dicarbonitrile. Preference is given to the use of carbonitriles in which $R^4$ of the general formula is a linear terminally bonded alkyl group containing at least 2 carbon atoms.

The use of the preferred carbonitriles offers an additional advantage—on top of the higher yields of 1,4-butanediol—in that the 1,4-butanediol formed separates from the reaction mixture and is therefore easy to recover. Optionally this separation from the reaction mixture can be further enhanced by the addition of other, phase separation promoting, solvents such as water, alcohols and aromatic hydrocarbons, such as benzene and toluene.

However, if desired, the reaction can also be carried out in a reaction medium which remains homogeneous, by using as solvent besides the carbonitrile solvent, for example an ether, such as diethyl ether, dioxane or tetrahydrofuran.

The quantity of carbonitrile solvent present in the reaction mixture may vary within wide ranges. Quantities of from about 1/10 mol carbonitrile per mol allyl alcohol may be used. Preferably the quantities of carbonitrile amount to 1/5 mol and more per mol allyl alcohol.

The carbon monoxide-hydrogen mixtures used in the process according to the invention may be very varied in composition. The carbon monoxide to hydrogen molar ratios may vary from 10:1 to 1:10. Preference is given to mixtures whose molar ratios lie between 5:1 and 1:5 and in particular to mixtures having molar ratios between 1:1 and 1:3. If required, the carbon monoxide to hydrogen molar ratio of the mixture used may be so altered during the course of the reaction as to range from an excess of carbon monoxide to an excess of hydrogen, in relation to the 1:2 carbon monoxide to hydrogen molar ratio which is the ratio in which carbon monoxide and hydrogen are consumed during the conversion of allyl alcohol into 1,4-butanediol.

In the carbon monoxide-hydrogen mixture inert gases, such as nitrogen, carbon dioxide, noble gases or methane can be included as diluent.

The process is carried out at temperatures lying between 20° C. and 200° C., preferably between about 30° C. and about 150° C. and in particular between about 50° C. and about 120° C. The overall pressure lies between about 1 and about 100 bar and in particular between about 20 and about 75 bar. High pressures, for instance of up to 1000 bar can be used, but generally they are unattractive for economic and technical reasons. The duration of the reaction is not critical and it is dependent on the temperature and pressure used. Generally the reaction time is 0.25 to 20 hours. Shorter or longer periods are not impossible, however.

The process according to the invention may be carried out batch-wise, continuously or semi-continuously. The reaction mixture obtained can be worked up by known techniques.

EXAMPLE I

Into a magnetically stirred Hastelloy C autoclave (Hastelloy is a trademark) of 300 ml content were placed 0.5 mol of a rhodium compound rhodium dicarbonylacetylacetonate or bis(rhodiumcarbonyl chloride), 10 ml allyl alcohol, 40 ml of a carbonitrile solvent and quantities of tri-n-alkylphosphines as described in Table A. The autoclave was flushed with carbon monoxide and charged with a mixture of carbon monoxide and hydrogen. The carbon monoxide and hydrogen partial pressures are 20 and 40 bar, respectively. The autoclave was heated for 5 hours at the temperatures given in Table A and then cooled. The two-phase system obtained whose bottom layer consisted of 1,4-butanediol was analyzed by gas-liquid chromatography. The total yield of 1,4-butanediol in a two-phase system was calculated on the quantity of allyl alcohol used as starting material.

TABLE A

| Exp. No. | Rhodium compound | Phosphine ligand (mmol) | Carbonitrile solvent | Temp. | Yield % |
|---|---|---|---|---|---|
| 1 | Rh(acac)(CO)$_2$ | (n-octyl)$_3$P (2.5) | decane carbonitrile | 75° C. | 40 |
| 2 | (RhCl(CO))$_2$ | (n-octyl)$_3$P (10) | heptane carbonitrile | 85° C. | 65 |
| 3 | Rh(acac)(CO)$_2$ | (n-butyl)$_3$P (15) | nonane carbonitrile | 95° C. | 69 |

EXAMPLE II

Into a magnetically stirred Hastelloy C autoclave (Hastelloy is a trademark) of 300 ml content were placed 0.5 mmol rhodium dicarbonylacetylacetonate, 10 ml allyl alcohol, 40 ml of a solvent and quantities of phosphines as described in Table B. The autoclave was flushed with carbon monoxide charged with a mixture of carbon monoxide and hydrogen. The carbon monoxide and hydrogen partial pressures were 20 and 40 bar, respectively. The autoclave was heated for 5 hours at 75° C. and then cooled. The reaction mixture obtained, which depending on the solvent used, either did or did not consist of a two-phase system due to separation of 1,4-butanediol (vide Table B) was analyzed by gas-liquid chromatography. The total yield of 1,4-butanediol present in the reaction mixture was calculated on the quantity of allyl alcohol used as starting material.

TABLE B

| Exp. No. | Phosphine ligand (mmol) | Solvent | Two-phase system yes/no | Yield % |
|---|---|---|---|---|
| 1 | (n-butyl)$_3$P (5) | octane carbonitrile | yes | 55 |
| 2 | (n-butyl)$_3$P (5) | acetonitrile | no | 10 |
| 3 | (n-butyl)$_3$P (5) | benzene | yes | 40 |
| 4 | (n-butyl)$_3$P (5) | n-decane | yes | 10 |
| 5 | (n-butyl)$_3$P (5) | N—methylpyrrolidone | no | — |
| 6 | (n-butyl)$_3$P (5) | benzyl carbonitrile | no reaction | |
| 7 | (cyclohexyl)$_3$P (5) | undecane carbonitrile | no | 0* |
| 8 | (benzyl)$_3$P (5) | heptane carbonitrile | no | 0* |
| 9 | (ethyl)$_2$(phenyl)P (10) | tridecane carbonitrile | yes | 20 |

*product substantially hydroxybutyraldehyde

Experiments 2 to 9 are comparative experiments; they do not comply with the process according to the invention. They demonstrate that for achieving good yields as well as the 1,4-butanediol separation from the reaction mixture, both the carbonitriles and the phosphines of the invention are necessary.

I claim:

1. In a process for the preparation of 1,4-butanediol by reaction of allyl alcohol with carbon monoxide and hydrogen in the presence of a soluble rhodium catalyst, a tertiary phosphine and a solvent, the improvement comprising (a) the tertiary phosphine is a phosphine of the general formula

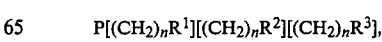

$$P[(CH_2)_nR^1][(CH_2)_nR^2][(CH_2)_nR^3],$$

wherein $R^1$, $R^2$ and $R^3$ each represent a linear terminally bonded alkyl group containing not more than 16 carbon atoms and n is 2 and at least 5 mol phosphine is used per gram atom rhodium, and (b) the solvent is a carbonitrile of the general formula $$R^4CH_2CH_2CH_2C\equiv N,$$

wherein $R^4$ represents an alkyl group containing 2 to 8 carbon atoms and the quantity of carbonitrile used per mol allyl alcohol is at least 1/5 mol.

2. A process as in claim 1, wherein $R^1$, $R^2$ and $R^3$ each are linear terminally bonded alkyl groups containing 2, 3, 4, 5 or 6 carbon atoms.

3. A process as in claim 1, wherein the reaction is carried out at temperatures between about 30° C. and about 150° C.

4. A process as in claim 1, wherein the reaction is carried out at an overall pressure between about 1 and about 100 bar.

* * * * *